United States Patent
Dekany et al.

(10) Patent No.: US 12,060,594 B2
(45) Date of Patent: Aug. 13, 2024

(54) SEPARATION OF 2'-FL FROM A FERMENTATION BROTH

(71) Applicant: Glycom A/S, Hørsholm (DK)

(72) Inventors: Gyula Dekany, Sinnamon Park (AU);
Györgyi Osztrovszky, Kisvárda (HU);
Martin Matwiejuk, Hamburg (DE);
Pierre Chassagne, Beaumont (FR);
Markus Jondelius Hederos, Trelleborg (SE)

(73) Assignee: Glycom A/S, Hørsholm (DK)

( * ) Notice: Subject to any disclaimer, the term of this patent is extended or adjusted under 35 U.S.C. 154(b) by 0 days.

(21) Appl. No.: 16/895,871

(22) Filed: Jun. 8, 2020

(65) Prior Publication Data

US 2020/0299740 A1   Sep. 24, 2020

Related U.S. Application Data

(63) Continuation of application No. 15/536,537, filed as application No. PCT/DK2015/050396 on Dec. 16, 2015, now Pat. No. 10,676,770.

(30) Foreign Application Priority Data

Dec. 16, 2014  (DK) .......................... PA 2014 70786

(51) Int. Cl.
*C12P 19/18*   (2006.01)
*C07H 1/06*    (2006.01)
*C07H 3/06*    (2006.01)

(52) U.S. Cl.
CPC ............... *C12P 19/18* (2013.01); *C07H 1/06* (2013.01); *C07H 3/06* (2013.01); *C12Y 204/01069* (2013.01)

(58) Field of Classification Search
CPC .. C12P 19/18; C07H 1/06; C07H 3/06; C12Y 204/01069
See application file for complete search history.

(56) References Cited

U.S. PATENT DOCUMENTS

| | | |
|---|---|---|
| 5,051,541 A | 9/1991 | Bawa et al. |
| 5,106,967 A | 4/1992 | Mazur |
| 2012/0208181 A1 | 8/2012 | Merighi |

FOREIGN PATENT DOCUMENTS

| | | |
|---|---|---|
| AU | 200062961 | 4/2001 |
| EP | 1405856 | 4/2004 |
| WO | 9640700 | 12/1996 |
| WO | 2005039299 A2 | 5/2005 |
| WO | 2010070104 A1 | 6/2010 |
| WO | 2010070616 A2 | 6/2010 |
| WO | 2011150939 A1 | 12/2011 |
| WO | 2012007481 A2 | 1/2012 |
| WO | 2012034996 A1 | 3/2012 |
| WO | 2012097950 A1 | 7/2012 |
| WO | 2012112777 A2 | 8/2012 |
| WO | 2013017330 A1 | 2/2013 |
| WO | 2013088267 A1 | 6/2013 |
| WO | 2014009921 A2 | 1/2014 |
| WO | 2014025560 A1 | 2/2014 |
| WO | 2014069625 A1 | 5/2014 |
| WO | 2014086373 A1 | 6/2014 |
| WO | 2015188834 A1 | 12/2015 |

OTHER PUBLICATIONS

Baumgartner, F. et al., "Construction of *Escherichia coli* strains with chromosomally integrated expression cassettes for the synthesis of 2'-fucosyllactose," Microbial Cell Factories, 2013, vol. 12(40).
Drouillard, S. et al., "Large-Scale Synthesis of H-Antigen Oligosaccharides by Expressing Helicobacter pylori 1,2-Fucosyltransferase in Metabolically Engineered *Escherichia coli* Cells," Angew. Chem. Int. Ed., 2006, vol. 45, pp. 1778-1780.
Lee, W. H. et al., "Whole cell biosynthesis of a functional oligosaccharide, 2'-fucosyllactose, using engineered *Escherichia coli*," Microbial Cell Factories, 2012, vol. 11(48).
Samain, E. et al., "Production of O-acetylated and sulfated chitooligosaccharides by recombinant *Escherichia coli* strains harboring different combinations of nod genes," Journal of Biotechnology, 1999, vol. 72, pp. 33-47.
Habova, V. et al., "Electrodialysis as a useful technique for lactic acid separation from a model solution and a fermentation broth," Desalination, 2004, vol. 163, pp. 361-372.

*Primary Examiner* — Paul J Holland
(74) *Attorney, Agent, or Firm* — Neal, Gerber & Eiseberg LLP

(57) ABSTRACT

The invention relates to a method for selective crystallization of 2'-fucosyllactose (2'-FL) from an aqueous solution comprising 2'-FL and one or more other fucosylated carbohydrates by adding acetic acid to the solution. The aqueous solution is separated from an aqueous culture medium prior to crystallization.

20 Claims, No Drawings

SEPARATION OF 2'-FL FROM A FERMENTATION BROTH

CROSS-REFERENCE TO RELATED APPLICATIONS

This application is a continuation of U.S. patent application Ser. No. 15/536,537, filed Jun. 15, 2017, now U.S. Pat. No. 10,676,770, which is a national stage entry pursuant to 35 U.S.C. § 371 of International Patent Application No. PCT/DK2015/050396, filed on Dec. 16, 2015, which claims priority to Denmark Patent Application No. PA 2014 70786, filed Dec. 16, 2014, the contents of all of which are fully incorporated herein by reference.

FIELD OF THE INVENTION

The invention relates to a method of selectively crystallizing 2'-O-fucosyllactose (2'-FL) from an aqueous solution containing also 2',3-di-O-fucosyllactose (DFL), using acetic acid, particularly from an aqueous solution from a biotechnological production of 2'-FL. The invention quite particularly relates to the crystallization of 2'-FL, so that the residual acetic acid content in the 2'-FL crystals, so produced, is less than 1 wt %.

BACKGROUND OF THE INVENTION

Many procedures are known for the biotechnological production of 2'-FL such as by fermentation with transformed *E. coli*. Some of them have been investigated only with qualitative analytical methods without mentioning the yield of 2'-FL or how to isolate it from the fermentation broth (WO 2010/070104, WO 2012/007481, Lee et al. *Microb. Cell Fact.* 11:48 (2012)). Preparative methods have been performed in lab scale and not exceeded a final titre of 25 g/l of 2'-FL (Drouillard et al. *Angew. Chem. Int. Ed.* 45, 1778 (2006); M. Randriantsoa: *Synthèse microbiologique des antigènes glucidiques des groupes sanguins,* Thèse de Doctorat soutenue le 30 Sep. 2008 à l'Universitè Joseph Fourier, Grenoble, France; WO 2012/097950, WO 2012/112777; Baumgärtner et al. *Microb. Cell Fact.* 12:40 (2013)). According to these publications, 2'-FL has been isolated from the aqueous culture medium or supernatant, in which the *E. coli* was fermented, by:
- separating the supernatant containing the product by centrifugation,
- adsorption of 2'-FL on a bed of activated charcoal that was washed with water to eliminate water-soluble contaminants like salts, amino acids and protein fragments,
- eluting 2'-FL with alcohol or aqueous alcohol, and then
- separating 2'-FL from other carbohydrates like lactose and fucose by gel permeation chromatography or flash chromatography on charcoal-celite bed.

The main drawback of this isolation method has been the need for chromatographic separation in order either to get pure 2'-FL or to obtain at least a mixture that is enriched in 2'-FL but still contains undesired derivatives. Although repeated chromatographic separations can result in the improvement of the purity, their high cost and relatively long times to handle the feed solution and the column packing, to carry out the separation and optionally to regenerate the packing, especially in large or industrial scale, can be disadvantageous and bothersome.

Crystallization or recrystallization is one of the simplest and cheapest methods to isolate a product from a reaction mixture, separate it from contaminations and obtain pure substance. Isolation or purification that uses crystallization makes the whole technological process more robust and cost-effective and thus advantageous. In this regard, WO 2011/150939 discloses obtaining anhydrous 2'-FL polymorphs I and II, and WO 2014/086373 discloses crystallizing 2'-FL, using methanol, from a freeze dried powder, derived from an aqueous fermentation broth. Moreover, WO 2014/009921 discloses, using acetic acid, to crystallize 2'-FL sesquihydrate from an aqueous solution, or crystallize anhydrous 2'-FL polymorph I from a dried 2'-FL syrup where the 2'-FL, in both cases, was produced by a hydrogenation reaction.

However, because of the byproducts produced in the aqueous culture medium during fermentation of 2'-FL, there has been a continuing need for an efficient process for crystallizing 2'-FL from the aqueous culture medium.

SUMMARY OF THE INVENTION

The invention relates to a method for selective crystallization of 2'-FL from an aqueous solution comprising 2'-FL and one or more other fucosylated carbohydrates, particularly one or more other monofucosylated and/or multifucosylated lactoses, more particularly one or more difucosylated lactoses, especially DFL, and optionally lactose, by adding acetic acid to the solution. Advantageously in this method, the aqueous solution was previously separated from an aqueous culture medium, in which the 2'-FL and DFL were produced by a genetically modified cell. Also advantageously in this method, the solution has a carbohydrate content of more than 50 w/w %, preferably more than 55 w/w %, more preferably more than 60 w/w %, particularly 62-68 w/w % with a 2'-FL/DFL ratio of more than 2:1, more preferably more than 4:1, even more preferably more than 6:1, particularly between 8:1 and 12:1. Also advantageously in this method, at least 2-10 litres, preferably 3-9 litres, more preferably 4-8 litres, of acetic acid are used per kilogram of 2'-FL in the solution.

By this method, 2'-FL can be crystallized with: i) a yield of at least 70%, preferably at least 85%; ii) a purity of at least 92%, preferably at least 95%; iii) a DFL content of less than 3%, preferably less than 2%; and iv) an acetic acid content of less than 3%, preferably less than 2%.

Also advantageously, 2'-FL is selectively crystallized from the solution by adding the acetic acid continuously or in portions to the solution over a period of 5 to 90 hours, preferably 10 to 40 hours, more preferably 15 to 30 hours, particularly about 20 to 25 hours. Preferably, about 25-50% of the acetic acid is added initially, and the rest is added in several, preferably 2-4 portions. By this method, 2'-FL crystals can be obtained with a residual acetic acid content of less than 1%, preferably no more than 0.5%.

DETAILED DESCRIPTION OF THE INVENTION

As a result of recent developments in producing 2'-FL by culturing genetically modified *E. coli,* aqueous fermentation broths have been produced with a significantly higher titre of 2'-FL, e.g. at least 75 grams, preferably at least 100 grams, more preferably at least 115 grams of 2'-FL per liter of the culture medium. However, fucosylated carbohydrates other than 2'-FL, particularly DFL, have also been found as by-products in such high-titre aqueous fermentation broths in a DFL/2'-FL ratio of 2:8 to 1:9 by weight. The fucosylated carbohydrates other than 2'-FL, in the aqueous solution, can be any other monofucosylated lactoses that can be formed during fermentation as a result of a deficient, defective or impaired fucosylation other than an α-1,2-fucosylation on the galactose moiety of lactose (e.g. one leading to 3-O-fucosyllactose, 3-FL), or of fucose migration of 2'-FL under the cultivation condition or post-fermentive operations, or of fucose hydrolysis from multifucosylated, preferably difucosylated, lactose. Such an other fucosylated lactose can also be a multifucosylated, preferably difucosylated, lactose that can be formed as a result of overfucosylation of lactose under the cultivation condition. The difucosylated lactose is preferably 2,2'-di-O-fucosyllactose or 2',3-di-O-fucosyllactose (DFL), particularly DFL as a characteristic by-product formed in a fermentative production of 2'-FL. This aqueous solution can also contain carbohydrate-like contaminants like 2'-0-fucosyl lactulose, lactose, lactulose, fucose, glucose, galactose and the like. These contaminants can be formed during fermentation or in post-fermentive purification/isolation steps, e.g., by rearrangement (e.g. 2'-O-fucosyl lactulose, lactulose) or by hydrolysis (e.g. fucose, glucose, galactose, lactose), or can be unconsumed educts or ingredients added during the fermentation (e.g., glucose as a carbon source). These contaminants are typically in a concentration of not more than 1-2 w/w % (individually), or 5-7 w/w % (altogether) in the aqueous solution. The aqueous solution typically can further contain up to 15 w/w %, preferably up to 10 w/w %, more preferably no more than 5 w/w %, particularly no more than 1 w/w %, of lactose as unused acceptor added to the fermentation broth.

It has now been discovered that 2'-FL can be selectively crystallized from an aqueous solution, obtained from such a high titred fermentation broth and containing 2'-FL and at least one fucosylated carbohydrates other than 2'-FL, particularly DFL, and optionally other carbohydrate-like contaminants, by treating the aqueous solution with acetic acid. This selective crystallization is particularly advantageous and surprising when the aqueous solution also contains other fucosylated carbohydrates and lactose. This selective crystallization provides 2'-FL of high purity in one step, and typically crystallization of batches of at least 100 g of 2'-FL, such as at least 1 kg, or at least 100 kg, or even at least 1 ton of 2'-FL, can be achieved despite the wide range of concentrations of contaminating sugar-like compounds in such aqueous solutions. In this regard, 2'-FL can be crystallized with a yield of at least 70%, preferably at least 85%. The purity of crystallized 2'-FL can be at least 92%, preferably at least 95%. In particular, the content of other fucosylated carbohydrates, particularly DFL, produced during the fermentation, can be less than 3%, preferably less than 2%, in the 2'-FL crystals, and the acetic acid content of the 2'-FL crystals can be less than 3%, preferably less than 2%. The resulting crystalline 2'-FL is preferably an anhydrous 2'-FL, particularly 2'-FL polymorph II as described in WO 2011/150939.

In a preferred embodiment, the aqueous solution described above, to be treated with acetic acid, has a carbohydrate content of more than 50 w/w %, preferably more than 55 w/w %, more preferably more than 60 w/w %, particularly around 62-68 w/w %, and the carbohydrate content of the aqueous solution has a 2'-FL/DFL ratio of more than 2:1, preferably more than 4:1, more preferably more than 6:1, particularly between 8:1 and 12:1. Alternatively, the 2'-FL concentration in the aqueous solution described above, to be treated with acetic acid, is 550-700 g/l, preferably 590-670 g/l. The above concentration ranges and ratios can be achieved in a conventional manner by concentrating an aqueous supernatant from the fermentation broth, preferably after removing, e.g. cells, proteins, protein fragments, DNA, caramelized by-products, salts and/or charged molecules from the fermentation broth. Concentration of the supernatant can be achieved in a conventional manner, e.g. by distilling water off at reduced pressure (20-100 mbars) and at ambient temperature up to 40-60° C. or by nanofiltration.

To the resulting aqueous solution, acetic acid, between room temperature (ca. 25° C.) and 50° C., is added, preferably at room temperature. The aetic acid is added continuously or in portions to the aqueous solution over a period of 5 to 90 hours, preferably 5 to 50 hours, more preferably 10 to 40 hours, even more preferably 15 to 30 hours, particularly about 20 to 25 hours. If the acetic acid is added at higher temperature (e.g. at around 50° C.) the period of its addition can be shorter: 5 to 20 hours, preferably 8 to 15 hours. Also preferably, the aqueous solution is continuously stirred at the same temperature while the acetic acid is being added and preferably thereafter while crystallization occurs. Crystallization is preferably initiated by adding 2'-FL seeding crystals to the aqueous solution, preferably within the first 2 to 5 hours of adding acetic acid to the aqueous solution.

Preferably, about 2-10 ml glacial of acetic acid is used for each 0.5-2.0 grams, particularly for each 1 gram, of 2'-FL in the aqueous solution. Thus, for an aqueous solution of 550-700 grams/liter of 2'-FL, preferably 590-670 grams/liter of 2'-FL, the carbohydrate content of which is more than 50 w/w %, at least about 2-10 litres, preferably 3-9 litres, more preferably 4-8 litres, particularly 5-7 litres, of acetic acid are used per kilogram of 2'-FL in the aqueous solution.

When 2'-FL is selectively crystallized from the aqueous solution by adding the acetic acid continuously or in portions, preferably by adding about 25-50%, particularly 50%, of the acetic acid initially and the rest in several, preferably 2-3, equal portions, to the solution over a period of 5-50 hours, preferably 10-40 hours, more preferably 15-30 hours, particularly about 20-25 hours, 2'-FL crystals can be obtained with a residual acetic acid content of less than 1 wt %.

Yet preferably, 2'-FL can be selectively crystallized from the aqueous solution by adding the acetic acid in portions, preferably 4-5 portions, to the solution over a period of 60-90 hours, and 2'-FL crystals can be obtained with a residual acetic acid content of less than 1 wt %, particularly no more than 0.5%.

The 2'-FL crystals so obtained are larger, therefore more easily filterable compared to previous 2'-FL crystals, particularly 2'-FL polymorph II.

The aqueous solution, from which 2'-FL can be selectively crystallized by acetic acid and which contains 2'-FL and one or more other fucosylated carbohydrates, preferably at least DFL, is preferably produced by a process comprising the steps of:
  i) culturing, in an aqueous culture medium containing lactose, a genetically modified cell, preferably an *E. coli* cell, that has been transformed with a recombinant gene encoding an α-1,2-fucosyl transferase and that can make 2'-FL by fucosylating lactose, to produce a fermentation broth containing 2'-FL and the other fucosylated carbohydrate, particularly DFL; and
  ii) separating non-carbohydrate particulates and contaminants from the fermentation broth.

Step ii) in the above process can include a conventional demineralization step during which minerals, salts and other charged molecules are extracted from the fermentation broth (containing 2'-FL and the other fucosylated carbohydrate) to make the aqueous solution, from which 2'-FL is to be crystallized. The demineralization can be conducted using conventional ion exchange resins, e.g. passing the fermentation broth through a cation exchange resin in H$^+$-form and an anion exchange resin in free base form. The cation exchange resin is preferably a strong exchanger, and the anion exchange resin a weak exchanger. The ion exchange resins, besides removing salts and charged molecules from the broth, can physically adsorb proteins, DNA and colorizing/caramel bodies that optionally have been left in the broth after previous purification steps. Alternatively, the demineralization can be conducted by means of a conventional electrodialysis or a conventional membrane filtration/diafiltration system using an appropriate particle size cut-off. The solution obtained in any of the above ways can then be concentrated by either a conventional evaporation step or a conventional nanofiltration step.

In addition, step ii) in the above process can also include a conventional charcoal treatment, preferably before the demineralization step, to remove colour bodies and optionally water soluble biomolecules (e.g., nucleic acids, peptides, proteins, amino acids, exopolysaccharides and lipids), left from previous purification steps. Charcoal has a weaker affinity for carbohydrate compounds in aqueous medium than for some water-soluble lipophilic contaminants (e.g. proteins and amino acids containing lipophilic moieties, lipids and coloured aromatic bodies). Thus, the carbohydrates, free of the lipophilic contaminants on the charcoal, can be easily washed from the charcoal with (distilled) water. Moreover, step ii) in the above process can also include a conventional clarification step for removing cells, cells fragments and proteins after fermentation, preferably prior to the charcoal treatment described above. The clarification can be done in a conventional manner, e.g. by sedimentation in centrifuge producing a clarified or partially clarified supernatant solution. Alternatively, the fermentation broth can be subjected to ultrafiltration in a conventional manner to remove high molecular weight components. The semipermeable membrane used for ultrafiltrating a 2'-FL fermentation broth can suitably have a cut off of 5-50 kDa, preferably 10-25 kDa, more preferably around 15 kDa. Depending on the characteristics of the fermentation broth to be clarified combination of higher and lower cut off membranes (in this order) within the above given range can be employed. Optionally, centrifugation or ultrafiltration can be followed by nanofiltration, during which the aqueous solution containing 2'-FL and accompanying carbohydrates is concentrated in a conventional manner before it is treated with charcoal. In this nanofiltration step, its membrane can have a pore size that ensures retention of 2'-FL having a molecular weight of 488; so typically a 200-300 Da cut off membrane can be used.

Step i) in the above process preferably produces 2'-FL in high titre. An *E. coli* strain, particularly an *E. coli* LacZ$^-$Y$^+$ strain, is preferably used having only one recombinant glycosyl transferase which is an α-1,2-fucosyl transferase, preferably an α-1,2-fucosyl transferase encoded by the futC gene from *Helicobacter pylori*. For making a mixture of 2'-FL in high yield, the method preferably involves: a) providing the culture medium with a carbon and energy source and at least 50, preferably at least 75, more preferably at least 100, even more preferably at least 125 grams of lactose based on 1 liter of initial culture volume. The method also preferably involves: b) providing lactose to the culture medium for more than 4 days, preferably up to 7 days, preferably in a continuous manner. It is also preferred that the final volume of the culture medium is not more than three-fold, more preferably not more than two-fold, particularly less than two-fold of the volume of the culture medium before providing the lactose and the carbon and energy source, preferably glycerol to the culture medium.

The culturing step of the above method is preferably carried out with:
a first phase of exponential cell growth ensured by a carbon-based substrate, and
a second phase of cell growth limited by a carbon and energy source which is added continuously, together with the lactose that is also added continuously.

The *E. coli* is preferably cultured continuously, preferably for at least 4 days, particularly up to 7 days, but not more than about 9-10 days, preferably at a temperature of 30 to 35° C., and preferably with continuous agitation, continuous aeration and continuous feeding of the carbon and energy source and lactose. The so-produced fermentation broth preferably contains at least 75 grams, more preferably at least 100 grams, particularly up to about 115 grams per liter of fucosylated carbohydrates, including DFL in an amount of about 2.5-20 w/w % relative to 2'-FL.

EXAMPLES

Example 1—Producing a Fermentation Broth With 2'-FL in High Yield

Bacterial Strains and Inoculum Preparation:
Engineered *E. coli* was constructed from *E. coli* K strain in accordance with WO 01/04341 and Drouillard et al. *Angew. Chem. Int. Ed. Eng.* 45, 1778 (2006), by deleting genes that are liable to degrade lactose, the oligosaccharide products and their metabolic intermediates, inter alia the lacZ, lacA and wcaJ genes, maintaining manB, manC, gmd and wcaG genes involved in the GDP-fucose biosynthesis, and inserting *H. pylori* futC gene for α-1,2-fucosyl transferase, as only glycosyl transferase.
Fermentation Condition:
Glucose, glycerol, isopropyl thio-β-D-galactopyranoside (IPTG) and lactose were each sterilized at 120° C.
The culture was carried out in a 3 l fermenter containing 1.5 l of mineral culture medium (Samain et al. *J. Biotechnol.* 72, 33 (1999)). The temperature was kept at 33° C. and the pH regulated at 6.8 with 28% NH$_4$OH. The inoculum (1% of the volume of the basal medium) consisted in a LB medium and the culture of the producing strain. The exponential growth phase started with the inoculation and stopped until exhaustion of the carbon source (glucose 17.5 g/l) initially added to the medium. The inducer (isopropyl thio-β-D-galactopyranoside, IPTG, 1-2 ml of a 50 mg/ml solution) was added at the end of the exponential phase. Then a fed-batch was realized, using 1 l of a feed solution containing 500 g of glycerol and 160-200 g of lactose dissolved in water, which was added to the culture during 4-7 days. At the end of the fermentation, the 2'-FL concentration in the fermentation broth varied between 68-114 g/l, and the 2'-FL/DFL ratio in the broth varied between around 80:20 to 92:8. Fucosylated lactulose (2'-O-fucosyl-lactulose) was no more than 1% in this broth.
Purification of the Fermentation Broth:
Cells and proteins were removed by ultrafiltration from the fermentation broth of Example 1, and the obtained solution was concentrated by nanofiltration. The solution was then treated with charcoal to decolorize. The decolorized solution was electrodyalised and concentrated at reduced pressure (20-30 mbars) and at 60° C. to tie required concentrations given in the examples below.

Example 2—Selective Crystallization of 2'-FL

A purified fermentation broth (100 ml, containing ≈22.6 g of 2'-FL, ≈2.2 g of DFL and ≈1 g of lactose, determined by HPLC) was concentrated to a ≈63 w/w % (all carbohydrate content) aqueous solution, to which glacial acetic acid (45 ml) was slowly added at room temperature. After addition of seeding crystal (100 mg) stirring was continued for about 3 hours while maintaining the temperature. Crystallization started. Then, 22.5 ml of acetic acid was slowly added to the slurry at room temperature with continued stirring for another 3 hours. Then, 22.5 ml of acetic acid was slowly added at room temperature to the slurry with continued stirring for another 17 hours. Solid white crystals were filtered off, washed twice with 10 ml of cold acetic acid and dried at 60° C. br 18 hours under vacuum (50 mbar) to give white crystals of 2'-FL polymorph II (19.6 g, 86%). HPLC assay: 95.6% 2'-FL, 0.67% DFL, 0.29% lactose, 0.79% acetic acid, 0.60% water.

Example 3—Selective crystallization of 2'-FL

The procedure of Example 2 was repeated with a different the way of adding glacial acetic acid to the aqueous solution. First, 33 ml of acetic acid was added slowly at room temperature followed by the addition of seeding crystal, then a second portion of acetic acid (12 ml) after 18 hours, a third portion of acetic acid (12 ml) in 3 hours, a fourth portion of acetic acid (12 ml) in 3 hours, and a fifth portion of acetic acid in 1.5 hours (21 ml), and stirring of the slurry was continued for 64 hours. After filtration, washing and drying, white crystals of 2'-FL polymorph II (19.4 g, 85%) were obtained. HPLC assay: 98.8% 2'-FL, 0.03% DFL, 0.09% lactose, 0.27% acetic acid, 0.73% water.

Example 4—Selective Crystallization of 2'-FL

A purified fermentation broth (600 ml, containing ≈173 g of 2'-FL and ≈17 g of DFL, determined by HPLC) was concentrated by removing water under vacuum to an aqueous solution having a 2'-FL concentration of ≈630 g/l. Glacial acetic acid (1.0 l) was slowly added, under agitation, at 35-45° C. After cooling the mixture to room temperature seeding crystal (100 mg) was added and the stirring was continued for 24 hours. Solid white crystals were filtered off, washed twice with 180 ml of cold acetone and dried at 40° C. under vacuum to give white crystals of 2'-FL polymorph II (166.6 g, 96%).

Example 5—Selective Crystallization of 2'-FL

A purified fermentation broth (200 ml, containing 2'-FL and DFL in a weight ratio of about 9:1) is concentrated to a ≈63 w/w % (all carbohydrate content) aqueous solution, to which glacial acetic acid (180 ml) is added at 40-45° C. over 75 min. Crystallization starts spontaneously. The suspension is allowed to cool down to room temperature and stirred for 2.5 days. Solid white crystals are filtered off, washed with aq. acetic acid and isopropanol, and dried to give white crystals of 2'-FL polymorph II (38.1 g, 84%).

The invention claimed is:
1. Crystalline 2'-O-fucosyllactose (2'-FL) derived from a fermentation broth and isolated using acetic acid, wherein the crystals of 2'-FL comprise less than 3% acetic acid by weight, wherein the crystalline 2'-FL is 2'-FL polymorph II,
wherein about 2-10 ml of acetic acid is used for each 0.5-2.0 grams of 2'-FL, and
wherein the crystals of 2'-FL are more easily filterable compared to crystals of 2'-FL polymorph II obtained in methanol crystallization.
2. The crystalline 2'-FL of claim 1, wherein the crystals of 2'-FL comprise at least 92% 2'-FL by weight.
3. The crystalline 2'-FL of claim 1, wherein the crystals of 2'-FL comprise at least 95% 2'-FL by weight.
4. The crystalline 2'-FL of claim 1, wherein the crystals of 2'-FL comprises less than 2% acetic acid by weight.
5. The crystalline 2'-FL of claim 1, wherein the crystals of 2'-FL comprises less than 1% acetic acid by weight.
6. The crystalline 2'-FL of claim 1, wherein the fermentation broth comprises 2'-FL and one or more other fucosylated carbohydrates, and wherein the one or more other fucosylated carbohydrates comprise 2',3-di-O-fucosyllactose (DFL), and
wherein the crystal of 2'-FL comprises less than 3% DFL by weight in the crystal.
7. Crystalline 2'-O-fucosyllactose (2'-FL) polymorph II crystallized from an aqueous solution comprising 2'-FL and one or more other fucosylated carbohydrates using acetic acid, wherein the one or more other fucosylated carbohydrates comprise 2',3-di-O-fucosyllactose (DFL) and wherein the crystals of 2'-FL polymorph II comprise less than 3% acetic acid by weight,
wherein about 2-10 ml of acetic acid is used for each 0.5-2.0 grams of 2'-FL, and
wherein the crystals of 2'-FL are more easily filterable compared to crystals of 2'-FL polymorph II obtained in methanol crystallization.
8. The crystalline 2'-FL polymorph II of claim 7, wherein the crystals of 2'-FL comprise less than 3% DFL by weight in the crystal.
9. The crystalline 2'-FL polymorph II of claim 7, wherein the crystals of 2'-FL comprise at least 92% 2'-FL by weight.
10. The crystalline 2'-FL polymorph II of claim 7, wherein the crystals of 2'-FL comprise at least 95% 2'-FL by weight.
11. The crystalline 2'-FL polymorph II of claim 7, wherein the crystals of 2'-FL comprises less than 2% acetic acid by weight.
12. The crystalline 2'-FL polymorph II of claim 7, wherein the crystals of 2'-FL comprises less than 1% acetic acid by weight.
13. Crystalline 2'-O-fucosyllactose (2'-FL), wherein the crystalline 2'-FL is 2'-FL polymorph II, obtained by a method of selective crystallization from an aqueous solution comprising 2'-FL and one or more other fucosylated carbohydrates, wherein the one or more other fucosylated carbohydrates comprise 2',3-di-O-fucosyllactose (DFL), the method comprises:
providing a fermentation broth, in which the 2'-FL and DFL have been produced by a genetically modified cell,
separating non-carbohydrate particulates and contaminants from the fermentation broth thereby providing the aqueous solution,
adding acetic acid to the aqueous solution to crystallize 2'-FL as crystals of 2'-FL polymorph II with a DFL content of less than 3% and/or an acetic acid content of less than 3% by weight,
wherein about 2-10 ml of acetic acid is used for each 0.5-2.0 grams of 2'-FL, and wherein the crystals of 2'-FL are more easily filterable compared to crystals of 2'-FL polymorph II obtained in methanol crystallization.

14. The crystalline 2'-FL of claim 13, wherein the crystals of 2'-FL comprises less than 1% acetic acid by weight.

15. The crystalline 2'-FL of claim 14, wherein about 2-10 litres of acetic acid are used per kg of 2'-FL, and the aqueous solution has a carbohydrate content which is more than 50 w/w %.

16. The crystalline 2'-FL of claim 15, wherein the aqueous solution comprises the 2'-FL in a concentration of 550-700 g/l.

17. The crystalline 2'-FL polymorph II of claim 7, wherein about 2-10 litres of acetic acid are used per kg of 2'-FL, and the aqueous solution has a carbohydrate content which is more than 50 w/w %.

18. The crystalline 2'-FL polymorph II of claim 17, wherein the aqueous solution comprises the 2'-FL in a concentration of 550-700 g/l.

19. The crystalline 2'-FL of claim 13, wherein about 2-10 litres of acetic acid are used per kg of 2'-FL, and the aqueous solution has a carbohydrate content which is more than 50 w/w %.

20. The crystalline 2'-FL of claim 19, wherein the aqueous solution comprises the 2'-FL in a concentration of 550-700 g/l.

* * * * *